United States Patent [19]

Bonfils et al.

[11] Patent Number: 5,672,595
[45] Date of Patent: Sep. 30, 1997

[54] METHOD OF CONTROLLING MALE FERTILITY

[75] Inventors: Armelle Bonfils, Paris; Daniel Philibert, La Varenne Saint Hilaire, both of France

[73] Assignee: Roussel UCLAF, France

[21] Appl. No.: 570,134

[22] Filed: Dec. 11, 1995

Related U.S. Application Data

[62] Division of Ser. No. 401,078, Mar. 8, 1995, Pat. No. 5,554,604.

[30] Foreign Application Priority Data

Mar. 24, 1994 [FR] France ................... 94 03410

[51] Int. Cl.$^6$ .................................... A61K 31/58
[52] U.S. Cl. .................................... 514/176
[58] Field of Search .................................... 514/176

[56] References Cited

FOREIGN PATENT DOCUMENTS

| | | |
|---|---|---|
| 90803 | 1/1963 | France . |
| 90804 | 7/1963 | France . |
| 1338308 | 8/1963 | France . |
| 2640977 | 6/1990 | France . |
| 984028 | 2/1965 | United Kingdom . |
| 984029 | 2/1965 | United Kingdom . |

OTHER PUBLICATIONS

Journal of Pharmacy and Pharmacology, The Pharmaceutical Society of Great Britain, vol. 16, No. II D.D. Evans, et al., pp. 717–724.
Estrogenic Activities of Some 3–Alkoxyestra–1,3, 5(10)–trien–17Beta–ols, C. Liarakos, et al., pp. 1247–1249, vol. 84, Center for Theoretical Bio. May 1969.

Primary Examiner—Phyllis G. Spivack
Attorney, Agent, or Firm—Bierman, Muserlian and Lucas LLP

[57] ABSTRACT

A method of controlling male fertility in warm-blooded male animals comprising administering to male warm-blooded animals an amount of a compound selected from the group consisting of a compound of the formula

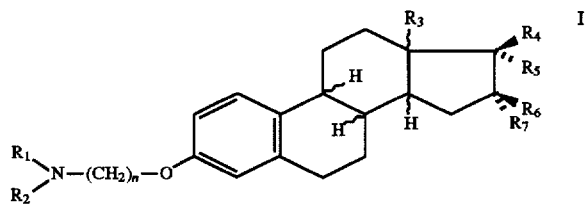

wherein $R_1$ and $R_2$ are taken together with the nitrogen to form a saturated 5 to 6 ring heterocycle, optionally containing a second nitrogen or oxygen in the ring, $R_3$ is α- or β-methyl, n is an integer from 2 to 10, $R_4$ and $R_5$ together are =O or $R_4$ is selected from the group consisting of hydrogen, —OH and acyloxy of an organic carboxylic acid of up to 12 carbon atoms and $R_5$ is selected from the group consisting of hydrogen, —OH, acyloxy of an organic carboxylic acid of up to 12 carbon atoms and alkyl, alkenyl and alkynyl of up to 8 carbon atoms, $R_6$ and $R_7$ together are =O or are individually selected from the group consisting of hydrogen, —OH and acyloxy of an organic carboxylic acid of up to 12 carbon atoms or $R_5$ and $R_6$ form a double bond and $R_4$ and $R_7$ are hydrogen and their non-toxic, pharmaceutically, acceptable acid addition salts in an amount sufficient to control male fertility.

8 Claims, No Drawings

METHOD OF CONTROLLING MALE FERTILITY

PRIOR APPLICATION

This application is a division of U.S. patent application Ser. No. 401,078 filed Mar. 8, 1995 now U.S. Pat. No. 5,554,604.

STATE OF THE ART

The compounds of formula I are known to possess antilipemic or hypocholesterolamic properties.

OBJECTS OF THE INVENTION

It is an object of the invention to provide a novel method of controlling fertility in male warm-blooded animals.

This and other objects and advantages of the invention will become obvious from the following detailed description.

THE INVENTION

The novel method of the invention of controlling male fertility in warm-blooded male animals comprises administering to male warm-blooded animals an amount of a compound selected from the group consisting of a compound of the formula

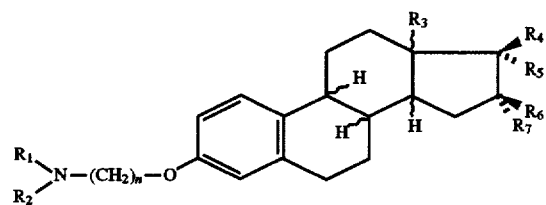

wherein $R_1$ and $R_2$ are individually selected from the group consisting of alkyl of 1 to 8 carbon atoms and benzyl or taken together with the nitrogen form a saturated 5 to 6 ring heterocycle optionally containing a second nitrogen or oxygen in the ring, $R_3$ is α- or β-methyl, n is an integer from 2 to 10, $R_4$ and $R_5$ together are =O or $R_4$ is selected from the group consisting of hydrogen, —OH and acyloxy of an organic carboxylic acid of up to 12 carbon atoms and $R_5$ is selected from the group consisting of hydrogen, —OH, acyloxy of an organic carboxylic acid of up to 12 carbon atoms and alkyl, alkenyl and alkynyl of up to 8 carbon atoms, $R_6$ and $R_7$ together are =O or are individually selected from the group consisting of hydrogen, —OH and acyloxy of an organic carboxylic acid of up to 12 carbon atoms or $R_5$ and $R_6$ form a double bond and $R_4$ and $R_7$ are hydrogen and their non-toxic, pharmaceutically acceptable acid addition salts in an amount sufficient to control male fertility.

Examples of $R_1$, $R_2$ and $R_5$ as alkyl of 1 to 8 carbon atoms include methyl, ethyl, propyl, isopropyl, butyl, isobutyl, tert-butyl, n-pentyl, n-hexyl, 2-methylpentyl, 2,3-dimethylbutyl, n-heptyl, 2-methylhexyl, 2,2-dimethylpentyl, 3,3-dimethyl-pentyl, 3-ethylpentyl, n-octyl, 2,2-dimethylhexyl, 3,3-dimethylhexyl and 3-methyl-3-ethylpentyl, preferably methyl, ethyl and isopropyl.

When $R_1$ and $R_2$ form with the nitrogen to which they are linked a saturated heterocycle with 5 or 6 members optionally containing another heteroatom chosen from oxygen and nitrogen, it is preferably piperidino, morpholino, piperazino or pyrrolidino.

Examples of acyloxy of an organic carboxylic acid of up to 12 carbon atoms acetyloxy, propionyloxy, butyryloxy, hexanoyloxy and benzoyloxy. Formyloxy can also be mentioned.

Examples of alkenyl having at most 8 carbon atoms are vinyl, allyl, 1-propenyl, butenyl, pentenyl or hexenyl and examples of alkynyl having at most 8 carbon atoms are ethynyl, propargyl, butynyl, pentynyl or hexynyl.

Examples of suitable acids for the non-toxic, pharmaceutically acceptable acid addition salts are hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane or ethane sulfonic acid, arylsulfonic acids such as benzene acid or p-toluene sulfonic acid and arylcarboxylic acids. Hydrochloric acid salts are preferred.

The wavy lines in positions 8, 9 and 14 indicate that the hydrogens are in position (8β,9α,14α) or (8α,9β,14β).

Among the preferred compounds of the invention are those wherein $R_3$ is a β-methyl, those of the formulae wherein $R_1$, $R_2$, $R_5$ and n are defined as above, those of the formula

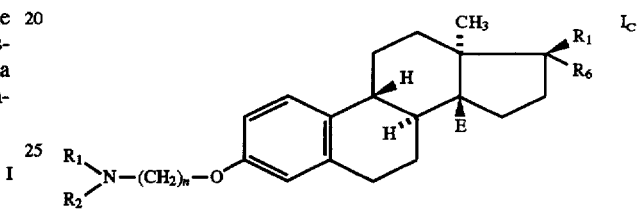

wherein $R_1$ and $R_2$ are individually alkyl of 1 to 8 carbon atoms, n is defined as above and either $R_4$ is hydrogen and $R_5$ is —OH or $R_4$ and $R_5$ together are =O or $R_4$ and $R_5$ are both hydrogen, those of the formulae

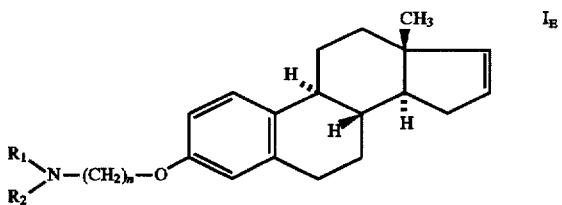

and

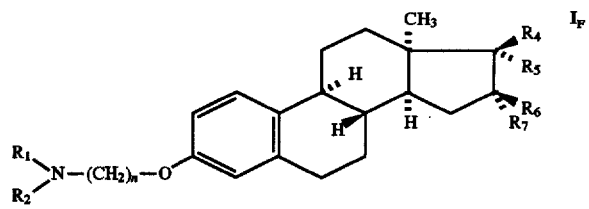

wherein $R_1$, $R_2$ and n are defined as above and either $R_4$ and $R_5$ together are =O or are individually selected from the group consisting of hydrogen, —OH and acyloxy of an organic carboxylic acid of up to 12 carbon atoms and $R_6$ and $R_7$ together form =O or are individually selected from the group consisting of hydrogen, —OH and acyloxy of an organic carboxylic acid of up to 12 carbon atoms or $R_5$ and $R_6$ form a double bond and $R_4$ and $R_7$ are hydrogen and their non-toxic, pharmaceutically acceptable acid addition salts.

More preferred compounds of formula I are those wherein $R_1$ and $R_2$ are both methyl or ethyl, those wherein n is 2 and their acid addition salts.

Specific preferred compounds of the invention are:
3-[2-(dimethylamino)-ethoxy]-$\Delta^{1,3,5(10)}$-estratrien-17-one,
3-[2-(diethylamino)-ethoxy]-$\Delta^{1,3,5(10)}$-estratrien-17-one,
3-[2-(dimethylamino)-ethoxy]-$\Delta^{1,3,5(10)}$-estratrien-17-one hydrochloride, 3-[2-(diethylamino)-ethoxy]-$\Delta^{1,3,5(10)}$-estratrien-17-one hydrochloride,
3-[2-(1-piperidinyl)-ethoxy]-$\Delta^{1,3,5(10)}$-estratrien-17-one,
3-[2-(4-morpholinyl)-ethoxy]-$\Delta^{1,3,5(10)}$-estratrien-17-one,
3-[3-(dimethylamino)-propoxy]-$\Delta^{1,3,5(10)}$-estratrien-17-one,
3-[3-(diethylamino)-propoxy]-$\Delta^{1,3,5(10)}$-estratrien-17-one,
3-[4-(dimethylamino)-butoxy]-$\Delta^{1,3,5(10)}$-estratrien-17-one,
3-[5-(dimethylamino)-pentyloxy]-$\Delta^{1,3,5(10)}$-estratrien-17-one,
3-[5-(diethylamino)-pentyloxy]-$\Delta^{1,3,5(10)}$-estratrien-17-one,
3-[10-(dimethylamino)-decyloxy]-$\Delta^{1,3,5(10)}$-estratrien-17-one,
3-[2-[methyl-(benzyl)-amino]-ethoxy]-$\Delta^{1,3,5(10)}$-estratrien-17-one,
3-[3-[bis(benzyl)-amino]-propoxy-$\Delta^{1,3,5(10)}$-estratrien-17-one,
(17β)-3-[2-[methyl-(benzyl)-amino]-ethoxy]-$\Delta^{1,3,5(10)}$-estratrien-17-ol,
(17β)-3-[3-(dimethylamino)-propoxy]-$\Delta^{1,3,5(10)}$-estratrien-17-ol,
(17β)-3-[3-(diethylamino)-propoxy]-$\Delta^{1,3,5(10)}$-estratrien-17-ol,
(17α)-3-[3-(diethylamino)-propoxy]-$\Delta^{1,3,5(10)}$-estratrien-17-ol,
(17α)-3-[2-(dimethylamino)-ethoxy]-$\Delta^{1,3,5(10)}$-estratrien-17-ol,
(17α)-3-[2-(diethylamino)-ethoxy]-$\Delta^{1,3,5(10)}$-estratrien-17-ol,
3-[2-(dimethylamino)-ethoxy]-$\Delta^{1,3,5(10)}$-estratrien-16-one,
3-[2-(diethylamino)-ethoxy]-$\Delta^{1,3,5(10)}$-estratrien-16-one,
3-[2-(diethylamino)-ethoxy]-$\Delta^{1,3,5(10)}$-estratrien-16-one hydrochloride,
3-[2-(dimethylamino)-ethoxy]-$\Delta^{1,3,5(10)}$-estratriene,
3-[2-(diethylamino)-ethoxy]-$\Delta^{1,3,5(10)}$-estratriene,
3-[2-(1-piperidinyl)-ethoxy]-$\Delta^{1,3,5(10)}$-estratriene,
3-[3-(1-piperidinyl)-propoxy]-$\Delta^{1,3,5(10)}$-estratriene,
3-[2-(diethylamino)-ethoxy]-$\Delta^{1,3,5(10)}$-estratriene hydrochloride,
3-[2-(4-morpholinyl)-ethoxy]-$\Delta^{1,3,5(10)}$-estratriene,
3-[2-(dimethylamino)-ethoxy]-$\Delta^{1,3,5(10),16}$-estratetraene,
3-[2-(diethylamino)-ethoxy]-$\Delta^{1,3,5(10),16}$-estratetraene,
(17α)-3-[3-(dimethylamino)-propoxy]-17-methyl-$\Delta^{1,3,5(10)}$-estratrien-17-ol,
(17α)-3-[2-(dimethylamino)-ethoxy]-17-methyl-$\Delta^{1,3,5(10)}$-estratrien-17-ol,
(17α)-3-[3-(dimethylamino)-propoxy]-19-nor-$\Delta^{1,3,5(10)}$-pregnatrien-17-ol,
(17α)-3-[2-(dimethylamino)-ethoxy]-19-nor-$\Delta^{1,3,5(10)}$-pregnatrien-17-ol,
(17α)-3-[2-[methyl(benzyl)-amino]-ethoxy]-19-nor-$\Delta^{1,3,5(10)}$-pregnatrien-17-ol,
(17α)-3-[3-(dimethylamino)-propoxy]-17-propyl-$\Delta^{1,3,5(10)}$-estratrien-17-ol,
(17α)-3-[3-(dimethylamino)-propoxy]-17-propyl-$\Delta^{1,3,5(10)}$-estratrien-17-ol hydrochloride,
(17α)-3-[3-(dimethylamino)-propoxy]-17-(1-propenyl)-$\Delta^{1,3,5(10)}$-estratrien-17-ol,
(17α)-3-[3-(dimethylamino)-propoxy]-17-(1-propenyl)-$\Delta^{1,3,5(10)}$-estratrien-17-ol hydrochloride,
(17α)-3-[2-(dimethylamino)-ethoxy]-19-nor-$\Delta^{1,3,5(10),20}$-pregnatetraen-17-ol,
(17α)-3-[3-(dimethylamino)-propoxy]-19-nor-$\Delta^{1,3,5(10),20}$-pregnatetraen-17-ol,
(17α)-3-[2-(dimethylamino)-ethoxy]-19-nor-$\Delta^{1,3,5(10)}$-pregnatrien-20-yn-17-ol,
(17α)-3-[3-(dimethylamino)-propoxy]-19-nor-$\Delta^{1,3,5(10)}$-pregnatrien-20-yn-17-ol,
(17α)-3-[3-(dimethylamino)-propoxy]-19-nor-$\Delta$1,3,5(10)-pregnatrien-20-yn-17-ol hydrochloride,
(17α)-3-[2-(diethylamino)-ethoxy]-19-nor-$\Delta^{1,3,5(10)}$-pregnatrien-20-yn-17-ol,
(17α)-3-[3-(diethylamino)-propoxy]-19-nor$\Delta^{1,3,5(10)}$-pregnatrien-20-yn-17-ol,
(17α)-3-[2-[methyl(benzyl)-amino]-ethoxy]-19-nor-$\Delta^{1,3,5(10)}$-pregnatrien-20-yn-17-ol,
(17α)-3-[2-[methyl(benzyl)-amino]-ethoxy]-19-nor-$\Delta^{1,3,5(10)}$-pregnatrien-20-yn-17-ol hydrochloride,
(17α)-3-[3-[methyl(benzyl)-amino]-propoxy]-19-nor-$\Delta^{1,3,5(10)}$-pregnatrien-20-yn-17-ol,
(8α,9β,13α,14β)-3-[2-(dimethylamino)-ethoxy]-$\Delta^{1,3,5(10)}$-estratrien-17-one,
(8α,9β,13α,14β)-3-[2-(diethylamino)-ethoxy]-$\Delta^{1,3,5(10)}$-estratrien-17-one,
(8α,9β,13α,14β)-3-[2-(dimethylamino)-ethoxy]-$\Delta^{1,3,5(10)}$-estratriene,
(8α,9β,13α,14β)-3-[2-(diethylamino)-ethoxy]-$\Delta^{1,3,5(10)}$-estratriene,
(8α,9β,13α,14β)-3-[2-(diethylamino)-ethoxy]-$\Delta^{1,3,5(10)}$-estratriene hydrochloride,
(8α,9β,13α,14β,17α)-3-[2-(diethylamino)-ethoxy]-$\Delta^{1,3,5(10)}$-estratrien-17-ol,
(13α)-3-[2-(dimethylamino)-ethoxy]-$\Delta^{1,3,5(10)}$-estratrien-17-one,
(13α)-3-[2-(diethylamino)-ethoxy]-$\Delta^{1,3,5(10)}$-estratrien-17-one,
(13α)-3-[2-(dimethylamino)-ethoxy]-$\Delta^{1,3,5(10)}$-estratriene,
(13α)-3-[2-(diethylamino)-ethoxy]-$\Delta^{1,3,5(10)}$-estratriene,
and their non-toxic, pharmaceutically acceptable acid addition salts.

The compounds of formula I are known and can be prepared by the processes described in British patents No. 984,028 and No. 984,029, U.S. Pat. No. 3,212,971, French patent No. 1,338,308 and French patents of addition No. 90,803 and No. 90,804.

It has now been found that the compounds of formula I have useful properties in the regulation of calcium flow in the spermatozoid. The products have 1) a strong affinity for the Sigma receptors (see pharmacological tests) and 2) an activity vis-à-vis the influx of the calcium into the spermatozoid.

Results of tests show that among the products which fix to the Sigma receptors, certain act by stimulating the influx of calcium into the spermatozoid, others by inhibiting the influx of calcium stimulated or not by progesterone, a molecule described as binding to the Sigma receptor. The products of formula I have an agonist activity and stimulate the influx of calcium into the spermatozoid. They can therefore be used in the treatment of certain forms of sterility characterized by an insufficient fertilizing power of the spermatozoids.

The products of formula I having an antagonist activity inhibit the influx of calcium into the spermatozoid. They are therefore useful for controlling the acrosomial reaction and consequently affect the fertilizing power of the spermatozoid. They can therefore be used as a contraceptive and in particular as a male contraceptive. They can also be used in the veterinary field as a male contraceptive in domestic animals (dogs, cats . . . ) or to limit the proliferation of any pests, in particular rodents or pigeons.

The useful dose varies as a function of the illness to be treated and the administration route. It can vary for example from 0.1 to 13 mg/kg per day in an adult man by oral route.

The compounds of formula I can be administered orally, rectally, parenterally or by local route, particularly for a woman, for example by percutaneous route, or by injection, in particular sub-cutaneous in the veterinary field.

They can be in the form of tablets, dragees, capsules, granules, suppositories, injectable preparations, pessaries, particularly vaginal pessaries and ointments, creams, gels, microspheres, implants and patches prepared by the usual methods.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

In the following examples, there are described several preferred embodiments to illustrate the invention. However, it should be understood that the invention is not intended to be limited to the specific embodiments.

PHARMACOLOGICAL TESTS

METHOD

Preparation of the Human Spermatozoids

The human sperm originated from healthy donors. The mobile spermatozoids were separated by centrifugation on a Percoll gradient (47.5–95%), then resuspended in a hypertonic BWW medium containing: 166 mM of NaCl, 5 mM of KCl, 1.3 mM of $CaCl_2$, 1.2 mM of $KH_2PO_4$, 1.2 mM of $MgSO_4$, 5.5 mM of glucose, 21 mM of sodium lactate, 0.25 mM of sodium pyruvate, 25 mM of $NaHCO_3$, 20 mM of Hepes and 0.8% of HSA (410 mosm/liter), pH 7.4 at ambient temperature.

Measurement of the Intracellular Calcium

The mobile spermatozoids were incubated for a minimum of 2 hours in the BWW/HSA capacitating medium. They were then incubated at a concentration of $5-10\times10^6$/ml with Fura2-AM (final concentration 2 µM) at 37° C. for 45 minutes. After washing by centrifugation for 10 minutes in BWW without HSA, the spermatozoids were resuspended at a concentration of $4\times10^6$/ml. The fluorescence signal was measured at 37° C. using a spectrofluorimeter at excitation wave lengths of 340 and 380 nm (PTIM 2001-Kontron) or at 340, 360 and 380 nm (Hitachi F 2000-B. Braun Science Tec.). The fluorescence emission was recorded at 505 nm. The progesterone or the product to be tested, dissolved in absolute ethanol, were added to the incubation medium at a final concentration of 0.1% of ethanol. When an antagonistic effect of the progesterone was found, the product was added to the medium 2 minutes before the progesterone. At the end of each dosage, 5 µM of ionomycin were added to the sample to measure the maximum fluorescence signal. Then, the spermatozoids were permeabilized with 0.05% of Triton X-100 and 10 mM of EGTA were added (pH 9.5) to measure the minimum fluorescence signal. These values allowed the intracellular concentration of calcium ($[Ca^{2+}]i$) to be calculated by the method described by Grunkiewicz et al, (1985) J. Biol. Chem., Vol. 260, pp. 3440–3450. The results of the intracellular calcium concentrations were expressed relative to the basal level which was arbitrarily set to equal to 1.

Sigma Receptor: Measurement of the Relative Bond Affinity

The relative bond affinity was evaluated for preparations of rat brain and testicle membranes.

Preparation of the membranes:

Male Sprague-Dawley rats originating from Iffa Credo and weighing approximately 200 g were used. The animals were sacrificed by decapitation and the brain and testicles were removed and homogenized in 10 to 25 volumes of 50 mM Tris-HCl buffer (pH 7.7) at 4° C., using an Ultrathurax. The homogenates were centrifuged at 30,000 g for 15 minutes at 4° C. The pellets were then washed 3 times by resuspension in the same buffer and centrifugation under the same conditions. The membranes obtained in this way were stored at −80° C.

Incubation:

The marker of the sigma receptors used was $^3H$ PPP (propyl-3-(3-hydroxyphenyl)-piperidine) of NEN having a specific activity of 3404 GBq/mmol. The membranes were resuspended in 50 mM of Tris-HCl buffer, pH 8.0 to obtain a concentration of proteins of approximately 0.6 mg/ml for the testicles and 1 mg/ml for the brain. Aliquots of the homogenate were incubated for 90 minutes at 25° C. in a total volume of 0.5 ml with 3 nM of $^3H$ PPP in the presence of increasing concentrations of reference product (haloperidol) or of the products to be tested. At the end of the incubation, the $^3H$ PPP bound to the membranes was separated from the free $^3H$ PPP by rapid filtration on Whatman GF/C filters pre-treated beforehand with 0.05% of polyethyleneimine. The precipitate was washed twice with 5 ml of Tris-HCl buffer and counting of the radioactivity was carried out after the addition of 20 ml of scintillating liquid Aqualyte (Baker).

Calculation of the relative bond affinity (RBA):

The following two curves were drawn: percentage of bound tritiated marker 100×B/BO as a function of the logarithm of the concentration of unlabelled reference product or as a function of the logarithm of the concentration of unlabelled test product. The straight line of the following equation was determined:

$$I_{50}=100\ (BO/BO+Bmin/BO)/2\ \text{i.e.}$$

$$I_{50}=100\ (1+Bmin/BO)/2=50(1+Bmin/BO)$$

BO=concentration of the bound tritiated marker in the absence of any unlabelled product.

B=concentration of the bound tritiated marker in the presence of a concentration X of unlabelled product.

Bmin=concentration of the bound tritiated marker in the presence of a large excess of the unlabelled reference product (5,000 nM).

The intersections of the straight line $I_{50}$ and the curves allowed the evaluation of the concentrations of the unlabelled reference product (CH) and of the unlabelled test product (CX) which inhibited by 50% the specific binding of the tritiated marker of the receptor. The relative bond affinity (RBA) of the test product was determined by the equation:

$$RBA=100\ (CH)/(CX).$$

The RBA of the haloperidol was arbitrarily set equal to 100.

| Relative bond affinity for the Sigma receptor | | |
|---|---|---|
| Products | Brain (rat) | Testicle (rat) |
| Haloperidol | 100.0 | 100.0 |
| Progesterone | 0.7 | 0.3 |
| Estrone | <0.06 | |
| (8α,9β,13α,14β)-3-[2-(dimethylamino)-ethoxy- | 23.0 | 0.5 |

-continued

Relative bond affinity for the Sigma receptor

| Products | Brain (rat) | Testicle (rat) |
|---|---|---|
| $\Delta^{1,3,5(10)}$-estratriene (product X) | 85.0 | 12.5 |
| 3-[2-(diethylamino)-ethoxy-$\Delta^{1,3,5(10)}$-estratrien-17-one (product W) | 28.0 | |
| 3-[2-(1-piperidinyl)-ethoxy]-$\Delta^{1,3,5(10)}$-estratrien-17-one | 39.0 | |
| (13α)-3-[2-diethylamino)-ethoxy]-$\Delta^{1,3,5(10)}$-estratrien-17-one | 54.0 | |
| 3-[2-(1-piperidinyl)-ethoxy]-$\Delta^{1,3,5(10)}$-estratriene | 28.0 | |
| (8α,9β,13α,14β)-3-[2-(diethylamino)-ethoxy-$\Delta^{1,3,5(10)}$-estratriene hydrochloride | 24.0 | |
| (17α)-3-[2-(diethylamino)-ethoxy]-19-nor-$\Delta^{1,3,5(10)}$-pregnatrien-20-yn-17-ol | | |

Increase in the concentration of intracellular calcium ($[Ca^{2+}]i$) induced by progesterone and product W

| | Progesterone ($10^{-5}$ M) | Product W ($10^{-5}$ M) |
|---|---|---|
| Exp. 1 | 4.25 | 3.56 |
| Exp. 2 | 6.60 | 2.55 |

These results were expressed relative to the basal level set equal to 1.

The initial base levels were Exp. 1=200 nm and Exp. 2=250 nm.

Effective dose of product X on ($[Ca^{2+}]i$) PRODUCT X

| | $10^{-7}$ M | $10^{-6}$ M | $5 \times 10^{-6}$ M | $10^{-5}$ M | $2 \times 10^{-5}$ M |
|---|---|---|---|---|---|
| Exp. 1 | 1.50 | 1.63 | 2.55 | 7.20 | 8.50 |
| Exp. 2 | 1.38 | 1.78 | 5.56 | 12.00 | 8.00 |

The results were expressed relative to the basal level set equal to 1.

Comparison of effects of progesterone at $10^{-5}$ and product X at $10^{-5}$ M on $[Ca^{2+}]i$ Mean ± SEM n = 3

| Progesterone | Product X |
|---|---|
| 4.90 ± 0.92 | 4.80 ± 0.92 |

The results were expressed relative to the basal level set equal to 1.

CONCLUSION

Effect on the Intracellular Calcium of Human Spermatozoids

Progesterone at the concentration of $10^{-5}$M induced a transitory increase of the $[Ca^{2+}]i$ followed by a second phase where the $[Ca^{2+}]i$ was slightly greater than the basal level.

Product X caused a dose-dependent increase of the $[Ca^{2+}]i$ which at $10^{-5}$M reached an intensity equal to that caused by progesterone. Contrary to what was observed with progesterone, this effect was prolonged over time.

Relative Bond Affinity (RBA) for the Sigma Receptor

The product X and progesterone were capable of displacing $^3$H PPP. The RBA's calculated using rat brain membranes have also been evaluated on testicles and are given in the table.

The differences observed between the RBA's at the level of the brain and testicles could be explained by a different distribution of the various types of sigma receptor sites between these two organs. Such products can therefore stimulate the acrosomial reaction in the case of the agonists such as product X and can therefore be used in certain forms of sterility characterized by an insufficient fertilizing power of the spermatozoids.

Various modifications of the method of the invention may be made without departing from the spirit or scope thereof and it is to be understood that the invention is intended to be limited only as defined in the appended claims.

What we claim is:

1. A method of controlling male fertility in warm-blooded animals comprising orally administering to male warm-blooded animals an amount of a compound selected from the group consisting of a compound of the formula

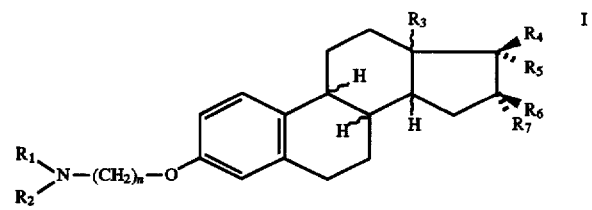

wherein $R_1$ and $R_2$ taken together with the nitrogen form a saturated 5 to 6 ring heterocycle optionally containing a second nitrogen or oxygen in the ring, $R_3$ is α- or β-methyl, n is an integer from 2 to 10, $R_4$ and $R_5$ together are =O or $R_4$ is selected from the group consisting of hydrogen, —OH and acyloxy of an organic carboxylic acid of up to 12 carbon atoms and $R_5$ is selected from the group consisting of hydrogen, —OH, acyloxy of an organic carboxylic acid of up to 12 carbon atoms and alkyl, alkenyl and alkynyl of up to 8 carbon atoms, $R_6$ and $R_7$ together are =O or are individually selected from the group consisting of hydrogen, —OH and acyloxy of an organic carboxylic acid of up to 12 carbon atoms or $R_5$ and $R_6$ form a double bond and $R_4$ and $R_7$ are hydrogen and their non-toxic, pharmaceutically acceptable acid addition salts in an amount sufficient to control male fertility by affecting the fertilizing power of the spermatozoids without hormonal activity.

2. The method of claim 1 wherein the compound is selected from the group consisting of a compound of the formula

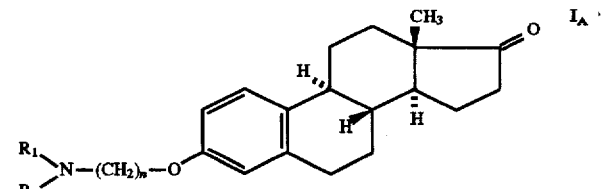

wherein the substituents are defined as in claim 1 and their non-toxic, pharmaceutically acceptable acid addition salts.

3. The method of claim 1 wherein the compound is selected from the group consisting of a compound of the formula

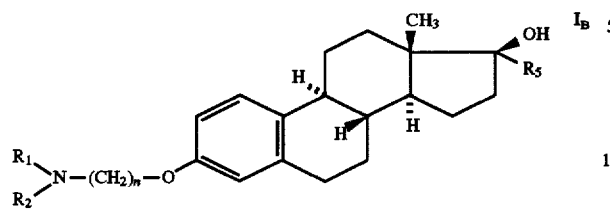

wherein $R_1$, $R_2$, $R_5$ and n have the definitions of claim 1 and their non-toxic, pharmaceutically acceptable acid addition salts.

4. The method of claim 1 wherein the compound is selected from the group consisting of a compound of the formula

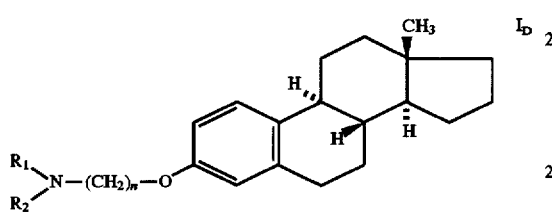

wherein $R_1$, $R_2$ are defined as in claim 1 and their non-toxic, pharmaceutically acceptable acid addition salts.

5. The method of claim 1 wherein the compound is selected from the group consisting of a compound of the formula

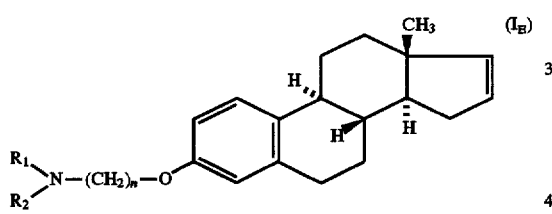

wherein $R_1$, $R_2$ and n are defined as in claim 1 and their non-toxic, pharmaceutically acceptable acid addition salts.

6. The method of claim 1 wherein the compound is selected from the group consisting of a compound of the formula

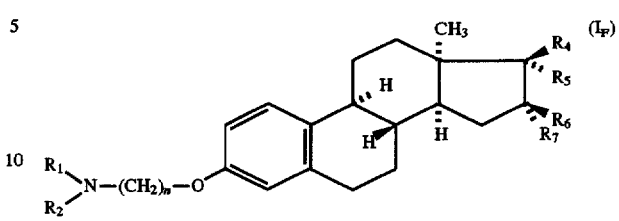

wherein $R_1$, $R_2$ and n are defined as in claim 1 and either $R_4$ and $R_5$ together are =O or are individually selected from the group consisting of hydrogen, —OH and acyloxy of an organic carboxylic acid of up to 12 carbon atoms, $R_6$ and $R_7$ together are =O or are individually selected from the group consisting of hydrogen, —OH and acyloxy of an organic carboxylic acid of up to 12 carbon atoms, or $R_5$ and $R_6$ form a double bond and $R_4$ and $R_7$ are hydrogen and their non-toxic, pharmaceutically acceptable acid addition salts.

7. The method of claim 1 wherein n is 2.

8. The method of claim 1 wherein the compound is selected from the group consisting of 3-[2-(1-piperidinyl)-ethoxy]-$\Delta^{1,3,5(10)}$-estratriene-17-one, 3-[2-(4-morpholinyl)-ethoxy]-$\Delta^{1,3,5(10)}$-estratriene-17-one, 3-[2-(1-piperidinyl)-ethoxy]-$\Delta^{1,3,5(10)}$-estratriene, 3-[2-(4-morpholinyl)-ethoxy]-$\Delta^{1,3,5(10)}$-estratriene, 3-[3-(1-piperidinyl)-propoxy-$\Delta^{1,3,5(10)}$-estratriene, and their non-toxic, pharmaceutically acceptable acid addition salts.

* * * * *